United States Patent
Boonen

(10) Patent No.: US 11,541,093 B2
(45) Date of Patent: Jan. 3, 2023

(54) **PHARMACOLOGICAL USE OF *CIMICIFUGA* EXTRACT**

(71) Applicant: Max Zeller Soehne AG, Romanshorn (CH)

(72) Inventor: Georg Boonen, Romanshorn (CH)

(73) Assignee: MAX ZELLER SOEHNE AG, Romanshorn (CH)

( * ) Notice: Subject to any disclaimer, the term of this patent is extended or adjusted under 35 U.S.C. 154(b) by 1067 days.

(21) Appl. No.: 14/412,535

(22) PCT Filed: Jul. 3, 2013

(86) PCT No.: PCT/EP2013/064062
§ 371 (c)(1),
(2) Date: Jan. 2, 2015

(87) PCT Pub. No.: WO2014/006104
PCT Pub. Date: Jan. 9, 2014

(65) Prior Publication Data
US 2015/0125555 A1    May 7, 2015

(30) Foreign Application Priority Data
Jul. 3, 2012    (CH) .................................. 01034/12

(51) Int. Cl.
*A61K 36/71* (2006.01)
*A61K 9/00* (2006.01)

(52) U.S. Cl.
CPC ............ *A61K 36/71* (2013.01); *A61K 9/0019* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 6,267,994 B1 | 7/2001 | Nesselhut et al. | |
| 6,303,586 B1 * | 10/2001 | McPeak | A21D 2/36 426/618 |
| 2005/0271756 A1 * | 12/2005 | Brattstrom | A61K 36/71 424/764 |

FOREIGN PATENT DOCUMENTS

| | | | |
|---|---|---|---|
| CN | 1 151 314 A | | 6/1997 |
| CN | 1151314 A | * | 6/1997 |
| CN | 101 537 071 A | | 9/2009 |
| DE | 2133080 A1 | * | 12/2009 |
| EP | 2 567 704 A1 | | 3/2013 |
| WO | WO 99/47149 | | 9/1999 |
| WO | WO 01/05415 | | 1/2001 |
| WO | WO 2005/002609 A1 | | 1/2005 |

OTHER PUBLICATIONS http://www.diabetes.org/diabetes-basics/genetics-of-diabetes.html.*
Herbslits May 21, 2011 http://www.herbslist.net/black-cohosh.html.*
Mayo Clinic, 2019, https://www.mayoclinic.org/diseases-conditions/type-2-diabetes/symptoms-causes/syc-20351193?p=1.*
PVP https://en.wikipedia.org/wiki/Polyvinylpyrrolidone (Year: 2021).*
Liu et al., Isoferulic Acid as Active Principle from the Rhizoma of Cimicifuga dahurica to Lower Plasma Glucose in Diabetic Rats, 1999, Planta Medica, 65: 712-714.*
Mukhopadhyay et al., Optimization of extraction process for phenolic acids from black cohosh (*Cimicifuga racemosa*) by pressurized liquid extraction, 2006, J Sci. Food Agric., 86: 156-162.*
Dan Seidlova-Wuttke et al: "Cimicifuga racemose and its triterpene-saponins prevent the Metabolic Syndrome and deterioration of cartilage in the knee joint of ovariectomized rats by similar mechanisms", Phytomedicine, vol. 19, No. 8-9, Jun. 1, 2012, pp. 846-853.
International Search Report of PCT/EP2013/064062, dated Aug. 7, 2013.
Jian-Xin Li et al: "Cimicifugae Rhizoma: From Origins, Bioactive Constituents to Clinical Outcomes", Current Medicinal Chemistry, Bentham Science Publishers BV, BE, vol. 13, Jan. 1, 2006, pp. 2927-2951.
Karin Kraft. Phytotherapeutische Optionen bei Diabetes mellitus Typ 2, Zeitschrift fur Phytotherapie. 2013. 34: 6-11.
Kiss Istvan et al: "Enhancement of organ regeneration in animal models by a stem cell-stimulating plant mixture", Journal of Medicinal Food Jun. 2010 Lnkd—Pubmed: 20406138, vol. 13, No. 3, Jun. 2010, pp. 599-604.

(Continued)

Primary Examiner — Terry A McKelvey
Assistant Examiner — Catheryne Chen
(74) Attorney, Agent, or Firm — Bryan D. Zerhusen, Esq.; Nicholas R. Herrel, Esq.; Cantor Colburn LLP

(57) ABSTRACT

The present invention relates to the novel use of an extract from a *Cimicifuga* species, preferably *Cimicifuga racemosa* (also termed *Actaea racemosa* L; black cohosh). In particular, the invention is directed to an extract from *Cimicifuga* sp., preferably *Cimicifuga racemosa*, for use in the therapeutic or prophylactic treatment of diabetes, preferably diabetes mellitus type 2, the use of such extracts for preparing a medicament, corresponding pharmaceutical compositions comprising the extract as well as a method for the therapeutic or prophylactic treatment of diabetes, preferably by oral administration of the extract or pharmaceutical composition.

7 Claims, 5 Drawing Sheets

(56) References Cited

OTHER PUBLICATIONS

Liu I-Min et al: "Isoferulic acid as active principle from the rhizome of Cimicifuga dahurica to lower plasma glucose in diabetic rats", Planta Medica, vol. 65, No. 8, Dec. 1999, pp. 712-714.
Rachon D. et al: "Effects of black cohosh extract on body weight gain, intra-abdominal fat accumulation, plasma lipids and glucose tolerance in ovariectomized Sprague-Dawley rats", Maturitas, Elsevier Science Publishers Ireland Ltd, IR, vol. 60, No. 3-4, Jul. 1, 2008, pp. 209-215.
Ruderman N et al. AMP kinase and malonyl-CoA: targets for therapy of the metabolic syndrome. Nat Rev Drug Discov. 2004. 3: 340-351.
Steinberg GR et al. AMPK in Health and Disease. Physiol Rev. 89 (2009) 1025-78.
Written Opinion of the International Searching Authority of PCT/EP2013/064062, dated Aug. 7, 2013.
Borrelli F et al. Cimicifuga racemose: a systematic review of its clinical efficacy. Eur J Clin Pharmacol. vol. 58 (2002), 235-241.

\* cited by examiner

PHARMACOLOGICAL USE OF *CIMICIFUGA* EXTRACT

CROSS-REFERENCE TO RELATED APPLICATIONS

The present disclosure is entitled to the benefit under 35 U.S.C. § 120 and 365(c) of International Patent Application PCT/EP2013/064062, entitled, "Novel Pharmacological Use of *Cimicifuga* Extract", filed, 3 Jul. 2013, which claims priority to Swiss Patent Application 01034/12, filed, 3 Jul. 2012, which are incorporated herein by reference in their entirety

FIELD OF THE INVENTION

The present invention relates to the novel use of an extract from a *Cimicifuga* species, preferably *Cimicifuga racemosa* (also termed *Actaea racemosa* L; black cohosh). In particular, the invention is directed to an extract from *Cimicifuga* sp., preferably *Cimicifuga racemosa*, for use in the therapeutic or prophylactic treatment of diabetes, preferably diabetes mellitus type 2, the use of such extracts for preparing a medicament, corresponding pharmaceutical compositions comprising the extract as well as a method for the therapeutic or prophylactic treatment of diabetes, preferably by oral administration of the extract or pharmaceutical composition.

BACKGROUND OF THE INVENTION

*Cimicifuga* extracts, their preparation as well as medical uses thereof are well-known. For example, WO 99/47149 describes the use of *Cimicifuga* extracts for use as organo-selective estrogen-type medicaments for selective treatment of cardiovascular diseases and climacteric discomfort. U.S. Pat. No. 6,267,994 discloses *Cimicifuga* extracts for use in anti-tumour therapy as compositions that do not exhibit the toxicity of high doses of anti-estrogenic compounds. WO 01/05415 discloses a pharmaceutical composition having an estrogen-type effect and containing components of *Cimicifuga* extract or derivatives. Phytomedicine, Vol. 19 (2012), p. 846-853 discloses special extracts from *Cimicifuga racemosa* that are capable of reducing body fat accumulation in rats.

WO 2005/002609 A1 teaches methods for the preparation of plant extracts, in particular from *Cimicifuga racemosa* using extraction agents together with solution mediators such as organic polymers, in particular poly(vinylpyrrolidone) that are useful for treating climacteric and post-menopausal distress.

Seidlova-Wuttke et al. (Phytomedicine, 19, 2012, 846-853) discloses the use of *Cimicifuga racemosa* extracts for reducing abdominal fat depots (hyperlipidemia) and thus preventing metabolic syndrome (MB) in ovariectomized (ovx) rats, mimicking a postmenopausal situation.

Kiss et al. (J. Med. Food, 13(3) 2010, 599-604) teaches regeneration of liver damage in a $CCl_4$-induced mouse model and pancreatic damage in an alloxan-induced experimental diabetes rat model by administration a complex dietary supplement of plant extracts called Olimpiq StemX-Cell (Crystal Institute Ltd., Hungary). The supplement comprises *Cimicifuga racemosa* as well as 8 further plant components. The administration of the dietary supplement resulted in faster and more efficient regeneration of both organs, which for the pancreas was indicated by reduction of blood sugar levels.

Rachon et al. (Maturitas 60, 2008, 209-215) teaches the effects of dietary *Cimicifuga racemosa* extract CR BNO 1055 on glucose tolerance (intraperitoneal glucose tolerance test, IPGTT), baseline glucose and fasting plasma insulin (FPI) in the menopause model using ovx rats. Contrary to the results of Kiss et al., which use the same extract and the same menopause model no statistically significant effect of the extract BNO 1055 on baseline blood glucose was observed and the extract lowered fasting plasma insulin similar to an estradiol (E2) control. And only E2 but not BNO 1055 administration resulted in a significant reduction of glucose AUC in the IPGTT. Even though the extract has an effect on glucose metabolism in ovariectomized rats this effect does not lower blood glucose as would be required for treating glucose-related disorders.

Liu et al. (Planta medica 65, 1999, 712-714) teaches that isoferulic acid extracted from the rhizome of *Cimicifuga dahurica* will lower plasma glucose levels in diabetic rats when applied intravenously at dosages of 5 and 10 mg/kg. However, the effect is very weak because no normalization of blood glucose could be obtained.

The Eur. J. Clin. Pharmacol., Vol. 58 (2002), 235-241 provides a systematic review of the clinical efficacy of *Cimicifuga racemosa* in many medical indications.

In her review article (Phytotherapeutische Optionen bei Diabetes mellitus Typ 2, Zeitschrift für Phytotherapie 2013; 34: 6-11) the author Karin Kraft summarizes current phytotherapeutic options for treating diabetes mellitus type 2 patients, however, a *Cimicifuga* product is not among the comprehensive list of phytotherapeutic agents.

The problem underlying the present invention is the provision of new medical indications for *Cimicifuga* plant products.

SUMMARY

It was surprisingly found that an extract from *Cimicifuga* species (sp.) has excellent utility for use in the therapeutic or prophylactic treatment of diabetes.

Therefore, in a first aspect, the invention is directed to an extract from *Cimicifuga* sp. for use in the therapeutic or prophylactic treatment of diabetes. Preferably, in the extract for practicing the invention the plant material from *Cimicifuga* sp. is from *Cimicifuga racemosa*. And in a preferred embodiment the extract of the invention is used for treating or preventing diabetes mellitus type 2 or it is used for the adjuvant treatment of insufficiently controlled insulin-dependent type 1 diabetes, In a more preferred embodiment, the extract for use in the invention is prepared by a method comprising the steps:

providing plant material from *Cimicifuga* sp., preferably *Cimicifuga racemosa*, treating the plant material with an extraction agent, and concentrating the extract.

It is preferred that the extract resulting from above steps (ii) is concentrated in the presence of a solution mediator, preferably an organic polymer capable of being colloidally dispersible or soluble in the extraction agent, more preferably an organic polymer having an average molecular mass of at least about 1000 Dalton units, most preferably polyvinylpyrrolidone (PVP).

In a most preferred embodiment of this aspect the extract for practicing the invention is made from *Cimicifuga racemosa* and the extract is for oral administration.

In a second aspect, the present invention relates to the use of an extract from *Cimicifuga* sp. for preparing a medicament for the therapeutic or prophylactic treatment of diabetes. It is preferred that for this use *Cimicifuga* sp. is *Cimicifuga racemosa*. It is further preferred for the claimed use that the disorder to be treated is diabetes mellitus type 2 or insufficiently controlled insulin-dependent type 1 diabetes, wherein the extract of the invention is used for adjuvant treatment. In a most preferred embodiment this aspect relates to a use wherein the extract is made from *Cimicifuga racemosa* and the extract is for oral administration.

In a third aspect, the present invention pertains to a pharmaceutical composition comprising an extract of the invention and optionally at least one pharmaceutically acceptable excipient for the therapeutic or prophylactic treatment of diabetes, preferably diabetes mellitus type 2 diabetes or insufficiently controlled insulin-dependent type 1 diabetes, wherein the extract of the invention is used for adjuvant treatment. It is preferred that the pharmaceutical composition of the invention is one wherein the *Cimicifuga* sp. is *Cimicifuga racemosa* and the extract is for oral administration.

In a fourth aspect the present invention reads on a method for the therapeutic or prophylactic treatment of diabetes, preferably diabetes mellitus type 2 or for the adjuvant treatment of insufficiently controlled insulin-dependent type 1 diabetes comprising administration of an extract of the invention or a pharmaceutical composition of the invention in a pharmaceutically effective amount.

In a preferred embodiment the composition of the invention is administered intravenously, intraperitoneally or orally, preferably orally.

In a very preferred embodiment relating to all aspects of the invention the extract for practicing the invention is obtained from plant material from *Cimicifuga racemosa*. In the following the invention will be detailed with reference to this species, however, the invention is not limited to this particular *Cimicifuga* species. While extracts of *Cimicifuga racemosa* obtained from various parts of that plant, e.g. from leaves, roots, stems, branches, or seeds, and/or by different extraction methods and extraction solvents are suitable for the invention, a preferred extract is one obtained from root material. Another preferred extract is one prepared according to the method disclosed in EP 1 644 015 mentioned above. Extracts of *Cimicifuga racemosa* prepared by other methods are suitable for the invention too.

BRIEF DESCRIPTION OF THE DRAWINGS

In the following examples and in the figures reference to percent or parts is based on weight unless specifically mentioned otherwise.

FIG. 2a shows the body weight increase of Ze 450 oral (PO) and intraperitoneal (IP) administration versus oral administration of vehicle (control).

FIG. 5a shows the effects of oral administration of Ze 450.

FIG. 6a shows the effects of oral administration of Ze 450.

DETAILED DESCRIPTION

Figure 1A:
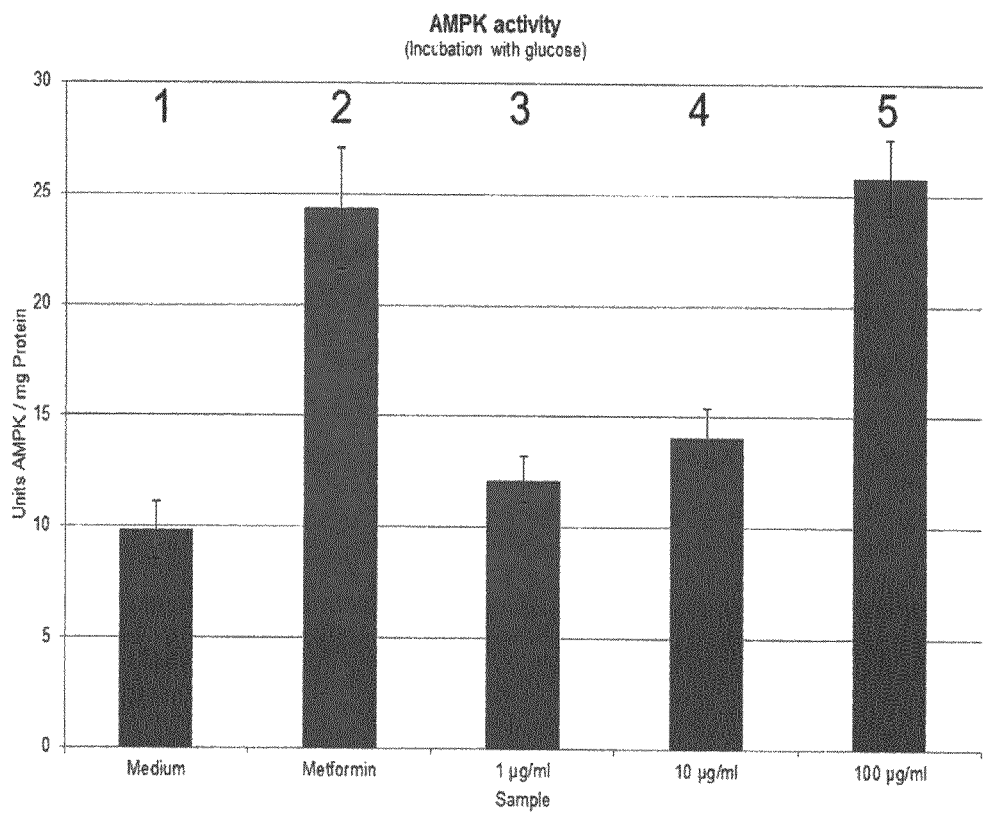
FIG. 1a is a diagram showing dose-dependent activation of AMPK by the extract of example 1 in dosages of 1, 10 and 100 μg/ml relative to medium control and metformin.

In general, methods of producing preferably *Cimicifuga racemosa* extracts are based upon treatment of plant material with an aqueous alkanolic extracting agent so as to obtain a raw or primary extract which, after an optional treatment for removal of fines, e.g. by sedimentation or filtration, so as to obtain a primary extract which contains the extracting agent and the plant constituents that are soluble in the extracting agent.

Typically, the primary extract is then concentrated by partial evaporation of the extracting agent so as to remove its more volatile components, e.g. an alkanolic constituent containing 1-4 carbon atoms in the alkanol group, plus some water, and to form what is called a concentrated extract, typically containing 5-50% by volume, of residual solvent, i.e. water. Upon further removal of solvent, a solid, pasty or liquid material is obtained that is substantially free of the solvent used for extraction of the plant material. This product can then be used as such or be processed to produce specific application forms, e.g. pills, lotions, solutions, powders etc., optionally adding whatever adjuvants, additives, coating components and the like are needed for the final medicinal product.

Generally, extracts from *Cimicifuga racemosa* suitable for the purposes of present invention will contain acteine, 23-epi-26-deoxyactein, 27-deoxyactin and cimiracemoside C. Actein is a xyloside of acetyl acteol with a 16,23:23,26:24,25-triepoxy side chain. 27-Deoxyactine is used as a standard for quantitative determination of the compounds mentioned above. A further known group of active ingredients are aromatic acids such as ferulic acid, hesperatinic acid and acyl caffeinic acid. Further, the following esters of hydroxy cinnamic acid have been isolated from aqueous ethanolic extracts of *Cimicifuga racemosa*: fucinolic acid and the cimicifugaic acids A, B, E and F. Flavonoides, biochanine A, formononetine and camphorol have also been reported. Other ingredients are tannins, resins and fatty acids (oleic acid, linolic acid, linolenic acid and palmitinic acid). It is noted that the content of ferulic acid in *Cimicifuga racemosa* is rather low.

With such a large number of constituents extraction conditions tend to have a substantial impact on the composition of the resulting extracts and any unintended change of the proportional makeup is undesirable.

Various additives, soluble or insoluble in the extraction agent, have been suggested and used to improve the concentration step in the preparation of the extract. While various additives such as organic acids or gelatine may be used to prevent unintended precipitation when concentrating the extract, the preferred additive, also termed "solution mediator" for use according to the present invention is polyvinylpyrrolidone as specified in the above mentioned EP 1 644 015.

The extract obtained by evaporation of the extracting solvent can be subjected to a further treatment for substantially removing any residual extraction agent, preferably by spray drying to obtain an essentially dry product.

The addition of PVP in a preferred embodiment of the present invention does not detract from using the extract in a medical treatment or as constituent of a medicament because PVP is admitted under current food and drug regulations for pharmaceutical use in most countries.

An effective amount of PVP as solution mediator generally is in the range of about 5% by weight to about 50% by weight based on the weight of the final extract. A range of about 15% by weight to about 35% by weight is preferred for many purposes.

The extraction agent is preferably a polar substance such as water and/or a normally liquid alkanol, e.g. methanol, ethanol, propanol, butanol. Mixtures of such $C_{1-4}$ alcohols with each other and/or with water are even more preferred. Mixtures of from about 40 to about 80% by weight of such an alkanol, preferably ethanol with about 60 to about 20%, by weight of water are particularly preferred.

The extraction procedure may be carried out in a conventional apparatus. In any case, the solution mediator is added prior to any significant removal of extraction agent. Such removal or concentration can be effected in a known manner, e.g. by distillation at an elevated temperature and/or reduced pressure taking care to avoid conditions that could affect the components of the extract. Concentration may be effected at constant or varying conditions of temperature and/or pressure.

A preferred way of producing the extract is carried out by extraction of the dry plant material with an ethanol-water mixture containing about 50-60% by volume of ethanol and about 50-40% by volume of water. Upon concentration the alkanolic constituents plus any water of an azeotropic mixture is removed until a solids concentration of about 25-50% by weight is reached. The concentrated extract obtained may then be processed in any conventional manner, e.g. by spray-drying to form a dry product. During such a final concentration step, e.g. upon spray-drying the solution mediator PVP additionally acts as a spray-drying adjuvant. Generally, the PVP has the effect that a homogeneous consistence of the extract is maintained in all stages of the concentration process.

An extract, pharmaceutical composition, i.e. medicament according to the invention normally contains the extract of *Cimicifuga* sp., preferably *Cimicifuga racemosa* in an amount suitable for administration with or without conventional and well-known components of medicaments which, in turn, may but need not be pharmaceutically active. On the other hand, an extract or pharmaceutical composition according to the invention may substantially consist of the novel extract, e.g. in a liquid or solid form and with or without a diluent.

An extract of *Cimicifuga racemosa* used for treatment according to the invention—e.g. for medical treatment or for preparation of a medicament—may have the clinical aim to treat or to prevent diabetes mellitus of type 2 and to serve as an adjuvant treatment for the insufficiently controlled type 1 diabetes.

While all types of application of the medicament are believed to be suitable according to the invention, oral administration is preferred for many purposes, and the extract can be used as such or in dilution with solid and/or liquid additives and/or contain additives or adjuvants and/or other pharmacologically active constituents. Preparation of pharmacologically suitable compositions is standard and does not require detailed explanation.

A preferred dosage is in the range of from about 1 to about 1000 mg of extract per day, preferably about 1 to about 200 mg/day, more preferred about 1 to about 100 mg/day, most preferred about 2 to about 50 mg/day, depending of course on the intensity of treatment required.

Generally, the term "extract" as used herein without further specification is intended to refer to any form of the product of extraction minus the extracting agent and regardless of the physical form (i.e. viscous, pasty or solid).

The term "diabetes" as used herein is intended to include diabetes mellitus of either type 1 (i.e. insulin-dependent) or type 2 (insulin-non-dependent).

The term "polyvinylpyrrolidone" is intended to include any PVP product admitted as a food or drug additive.

Numeric indications used herein and preceded by a qualifier such as "about" are intended to included a margin of error of ±50%, preferably ±20%.

AMP refers to adenosine monophosphate-activated protein. AMP-activated protein kinase (AMPK) is a well known enzyme (cf. PMID 10409121) of importance in connection with cellular energy homeostasis.

In the following the invention will be illustrated in more detail by practical examples and with reference to figures, none of which are to be interpreted as limiting the scope of the invention beyond the claims as appended.

EXAMPLES

Example 1—Extract Preparation

Dry root material of *Cimicifuga racemosa* (rhizome) was processed by milling to obtain a powder, and charges of material from different harvests were combined for homogeneity.

The extraction agent was prepared by mixing 1'330 parts of ethanol (96%, by volume) and 1'170 parts of de-ionized water. Extraction was performed on the basis of a ratio of 2'500 parts extraction agent per 500 parts of *Cimicifuga racemosa*.

Water and ethanol of ambient temperature were mixed in a container provided with a mechanical stirrer and a withdrawal port at the bottom of the container. The *Cimicifuga racemosa* powder was added with stirring and stirring was continued for 300 minutes. Then, the stirrer was stopped and the solids were allowed to settle which normally takes about 180 minutes and, in any case, was continued until a clear supernatant had formed above the sediment.

The clear supernatant was removed by means of a pump and collected in a separate container. The sediment was fed into a filter press to recover additional extraction liquid which is combined with the supernatant and the resulting mixture was fed through a filter into a mixing container provided with a stirrer and a weighing device. Then, polyvinyl-pyrrolidone (PVP; Plasdone® KW 29-32) was added in an amount of 33 parts per 100 parts of extraction liquid and stirring was continued until the PVP had dissolved and a clear brown liquid was obtained as a first product.

This product was fed into a standard-type two-stage concentrator plant type KV 102 EX (Unipektin AG, Eschenz, Switzerland), in which the extraction liquid including the PVP was concentrated by evaporation of the extraction agent to yield a dark brown concentrate having a concentration of at least about 9% solids which was then further concentrated to form a spissum extract having a solids content between about 18 and 26%. This concentrate was fed into a conventional spray-dryer to produce a dry extract in the form of a powder with a humidity content of not more than about 5% by weight.

Both the concentrated liquid extract ("spissum") as well as the dry pulverulent extract can be standardized as required and used as or in a medicament for preventing or treating diabetes mellitus type 1 or type 2 according to the invention, for example by producing tablets containing 5 to 50 mg extract and the usual solid diluents, additives, and adjuvants for the production of tablets having a final weight of about 100-200 mg.

Example 2—Extract Analysis

The dry extract from example 1 was a fine lightly brown powder having a characteristic smell. It contained various triterpene saponines and various triterpene glycosides as well as organic acids.

Analytical results of three batches prepared according to example 1 indicated that the extract contained 27-deoxyactein, the substance conventionally used for standardization of extracts of *Cimicifuga racemosa*.

Example 3—Extract AMPK-Activity

The effect of the extract of example 1 on the activation of AMP kinase was investigated in HepG2 cells. Cell medium was used as negative control, metformin as a 2 mM solution in cell medium was used as a positive control, while the test samples contained 1, 10 and 100 μg of the product of example 1 per ml of cell medium (1 μg/ml). The results are presented in FIG. 1 below where the ordinate indicates units of activated AMPK per mg of protein. The black bars on the abscissa indicate the activity values for pure medium (1), metformin (2), a well-known diabetes drug, and the activity values obtained with 1 μg (3), 10 μg (4) and 100 μg (5), respectively.

As apparent from FIG. 1*a*, the extract of example 1 resulted in a dose-dependent AMPK activating effect which is indicative of an improved metabolic control including anti-diabetes activity for both forms of diabetes mellitus (non-insulin-dependent (Type 2) diabetes mellitus and insulin-dependent (Type 1)) (see Nat Rev Drug Discov 3 (2004), 340-351 and Physiol Rev 89 (2009) 1025-1078) since both lead to disturbed glucose tolerance and elevated blood glucose levels.

Pharmaceutical compositions according to the invention containing or consisting of extract from *Cimicifuga racemosa* have medical utility for improving blood glucose homeostasis in a human patient by enhanced cellular glucose uptake and improved insulin receptor sensitivity and result in decrease in body weight.

Furthermore, pharmaceutical compositions according to the invention improve blood glucose in a human patient with disturbed glucose tolerance and prevent or delay conversion to definite diabetes mellitus.

Pharmaceutical compositions according to the invention are effective for treating diabetic symptoms in a human patient suffering from insulin-dependent Type 1 diabetes who has insufficiently controlled blood glucose and/or indications of a secondary insulin receptor resistance.

Example 4—Extract In Vivo Activity on Glucose Control and Body Weight in Male ob/ob Mice The effects of oral 7-day administration of a *Cimicifuga racemosa* extract prepared according to example 1 and designated Ze 450 on body weight, daily food and water intake as well as glucose control were investigated in male ob/ob mice as follows. The ob/ob mouse is a well-characterized and representative in-vivo model of obesity and diabetes in mammals, in particular humans, wherein both disorders are the result of a mutation in the ob gene which encodes leptin. In the study metformin was the positive control.

Test compound Ze 450 was formulated in a dosing vehicle (PEG300) using a salt factor of 1.25. It was formulated at the beginning of the study, aliquoted and stored in the fridge. Metformin was formulated in deionised water using a salt factor of 1.25. Metformin was prepared fresh each day immediately prior to dosing. Drugs were administered in a suitable dose volume of 3 ml/kg. Metformin and D-Glucose were supplied by RenaSci Ltd. Drug doses relate to the free base.

Sixty-eight male ob/ob mice (approx. 7/8 weeks of age; four spares; from Janvier, France) were singly housed with free access to standard diet (Harlan Teklad Global 2018 diet) and tap water ad libitum. All mice were maintained at 24±2° C. and 55±20% humidity on a reverse phase 16 h on/8 h off light-dark cycle (lights on approx. 17:30-09:30 h).

Animals were acclimatized to the facility for 1 week. During the second week a baseline protocol was established where animals were dosed with vehicle orally (n=50) or intraperitoneally (n=18) once daily (day −6 to 0). Prior baseline dosing animals were allocated by a statistician into two groups (n=50 and n=18) based on body weight. Dosing began at 08:45 each day so that about half of the animals were dosed prior to lights off and half after lights off (09:30). Body weight, food and water intake were recorded daily. During the baseline phase animals underwent blood sampling from the lateral tail vein (30 μl) with the sample taken into a lithium heparin-coated tube (Sarstedt CB300LH), i.e. a sample taken from freely feeding animals. Blood sampling started at 16:00. All blood samples were centrifuged immediately after collection and the plasma fraction was stored frozen (−80° C.) prior to subsequent determination of plasma glucose (in duplicate) and insulin (single replicate) using commercially available kits and reagents (Thermo Scientific Infinity glucose reagent TR15498, Alpco mouse ultrasensitive insulin kit 80-INSMSU-E10). Then, baseline treatment was continued. Towards the end of the baseline phase animals were allocated to 8 treatment groups on based on body weight, baseline food and water intake, as well as plasma glucose and insulin.

Body weight, food and water intake were measured daily from 6 days before dosing to 6 days after dosing started. Animals were fasted overnight on Day 6 for an oral glucose tolerance test (OGTT) on Day 7. The animals also had freely fed bleeds on Day −4 and Day 6. During the baseline phase animals in groups A and B were dosed with water PO (perorally). Animals in groups C to F were dosed with PEG300 (PO) until Day 0, when they were switched to 5% Tween 80, 5% PEG400, 90% saline. Animals 2, 4, 9, 11 and 13 (groups G and H) reacted badly to dosing with PEG300 intraperitoneally (IP) on Day −6, so other animals in these groups were dosed with saline IP on this day. From Days −5 to 0, animals in groups G and H were dosed IP with 5% Tween 80, 5% PEG400, 90% Saline.

Mice were dosed once daily orally or intraperitoneally (approximately 8/9 weeks of age at the first dose) for 7 days with vehicle or test drug as detailed below:

TABLE 1

| Group | Treatment | n |
|---|---|---|
| A | Vehicle (water PO 3 ml/kg) | 8 |
| B | Metformin (200 mg/kg PO in water) | 8 |
| C | Vehicle (PEG 300 PO 3 ml/kg) | 8 |
| D | Ze 450 (10 mg/kg PO in PEG300) | 8 |
| E | Ze 450 (30 mg/kg PO in PEG300) | 8 |
| F | Ze 450 (90 mg/kg PO in PEG300) | 8 |
| G | Vehicle (PEG 300 IP 3 ml/kg in 5% Tween 80, 5% PEG400, 90% Saline) | 8 |
| H | Ze 450 (30 mg/kg IP in 5% Tween 80, 5% PEG400, 90% Saline) | 8 |

All treatments were dosed orally by gavage or intraperitoneally once daily. During the treatment period food intake, water intake and body weight were recorded daily at the dosing session. After dosing the animals were examined and any overt behavior was recorded. Dosing began at 08:45 each day for all groups. On the afternoon of Day 6 blood samples were collected as described previously for the baseline phase. Animals underwent blood sampling in the fed state at 16:00. 30 µl blood were taken into a lithium heparin-coated tube (Sarstedt Microvette CB300 LH). Each sample was centrifuged immediately and plasma was dispensed into an aliquot tube. All plasma samples were frozen at −80° C. and subsequently assayed for glucose (in duplicate) and insulin (single replicate) content using commercially available kits and reagents. Subsequently food was removed from each animal.

The following morning (Day 7) the mice underwent an OGTT. Each animal was dosed with vehicle or test compound and after an appropriate interval (e.g. 60 minutes) the animal was dosed with D-glucose (2 g/kg PO). Baseline blood samples were taken immediately prior to compound dosing (time=−15 min) and immediately before the glucose load (time=0 min). Further blood samples were taken 15, 30, 45 and 60 minutes post glucose administration. All blood samples (30 µl) were taken from the tail vein. Blood samples were placed into lithium heparinised tubes (Sarstedt Microvette CB300 LH) and plasma separated by centrifugation. All plasma samples were frozen at −80° C. and subsequently assayed for glucose (in duplicate) and insulin (single replicate) using commercially available kits and reagents.

At the end of the OGTT (i.e. 2 hours post final dose) all animals from groups B, D, E, F and H were killed by a schedule 1 method and terminal blood samples were taken via cardiac puncture. Each terminal blood sample (0.6 ml) was placed in a lithium heparin collection tube (e.g. Sarstedt Multivette® 600LH). Blood samples were centrifuged and the plasma fraction (approx 250 µl) transferred into a labelled collection vial. Plasma was stored frozen at −80° C. until analysis. All other animals were terminated.

Body weights, food intake and water intake were expressed as mean values ±SEM. Body weight, body weight gain, daily and average food and water intake data and cumulative food intake were analyzed by ANCOVA with baseline as a covariate, followed by appropriate comparisons (two-tailed) to determine significant differences from the appropriate control group. $P<0.05$ was considered to be statistically significant. Baseline was set as Day 1 value for body weight or the average food or water consumption over the baseline period.

Plasma glucose and insulin data were analyzed by robust regression with treatment as a factor and bleeding order and baseline body weight and plasma glucose or insulin as covariates followed by appropriate comparisons (two-tailed) to determine significant differences from the appropriate control group. A log transformation was used if appropriate.

AUC 0 to 60 were calculated by trapezoidal rule (calculated as total AUC and AUC from baseline) and analyzed by the same methodology.

Figure 1B:
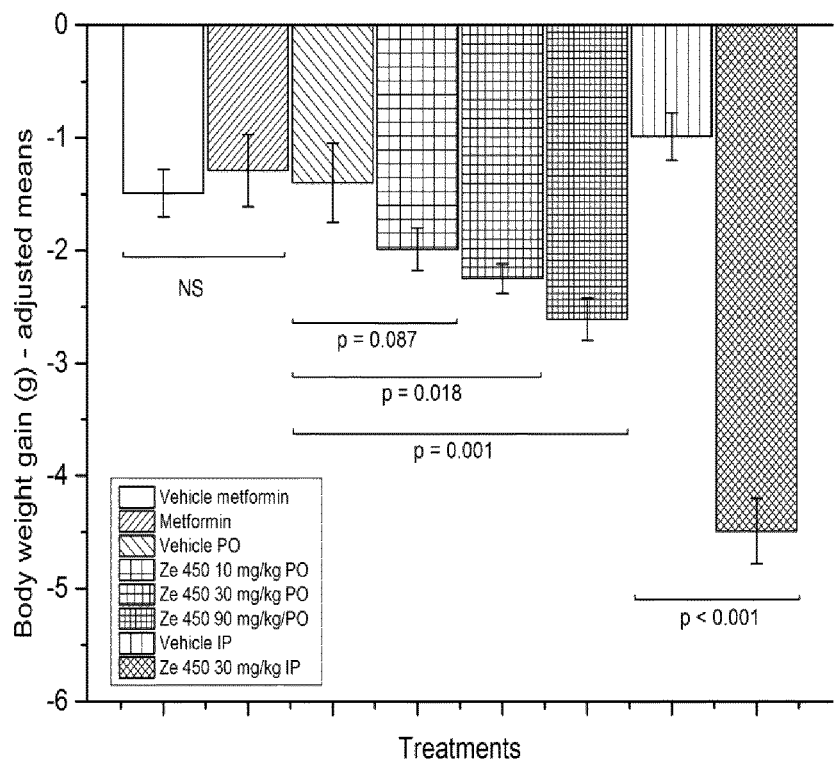
FIG. 1b is a diagram illustrating the overall changes in body weights (g) over days 1 to 7: Means are adjusted for differences between the treatment groups at baseline (day 1). Standard errors of the mean (SEM) are calculated from the residuals of the statistical model. Multiple comparisons against the appropriate vehicle are by Williams' test for Ze 450 PO, the multiple t test for Metformin and Ze 450 IP.

All treatments were well tolerated by the animals. Body weight was not statistically different between treatment groups during the baseline period. After 6 days of treatment, metformin had no significant effect on overall body weight (FIG. 1b). Compared to the oral control Ze 450 caused a significant and dose-dependent reduction in body weight (−1.99 to −2.61 g). The IP administration of 30 mg/kg Ze 450 showed the strongest reduction in body weight (−4.49 g; p<0.001).

Figure 2A:
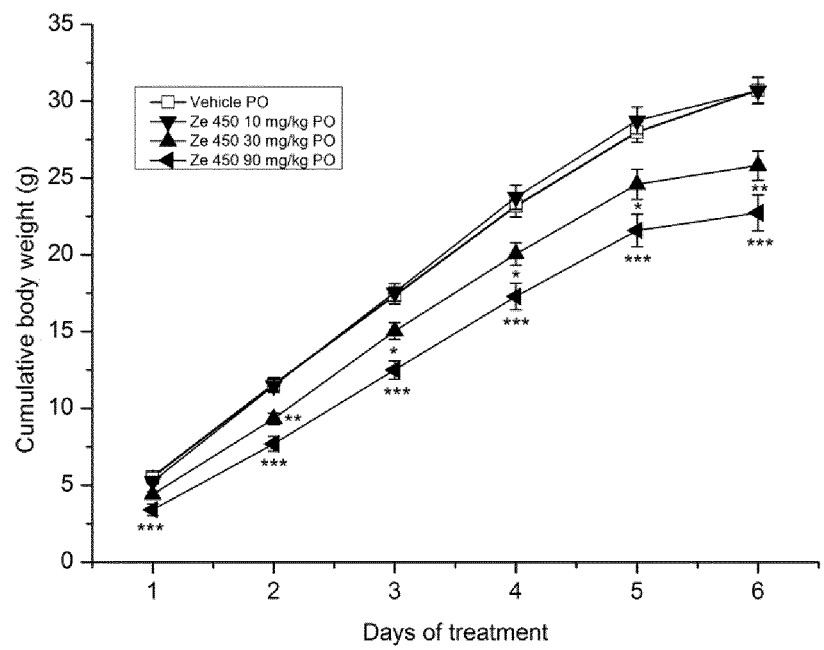
FIGS. 2a and b are graphs illustrating the cumulative increase in body weight over 6 days of treatment.
Figure 2B:
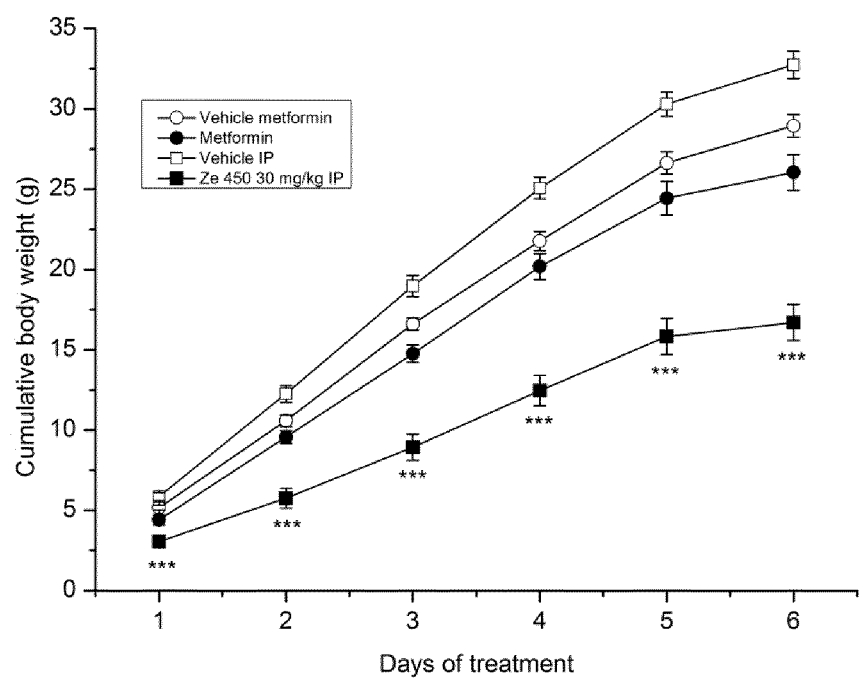
FIG. 2b shows the oral administration of metformin and IP administration of Ze 450 versus respective controls (significant differences vs. respective vehicles: $*p<0.05$, $p<0.01$, $*p<0.001$).

Cumulative body weight over the 6 treatment days showed a significant, dose-dependent reduction for Ze 450 given orally (see FIG. 2A). This decrease was significant for the two higher PO doses (e.g. 30 mg/kg and 90 mg/kg Ze 450). The largest reduction was observed in the treatment group where Ze 450 was given by IP injection. For metformin, virtually no reduction was seen compared to its control group (see FIG. 2B).

Figure 3:
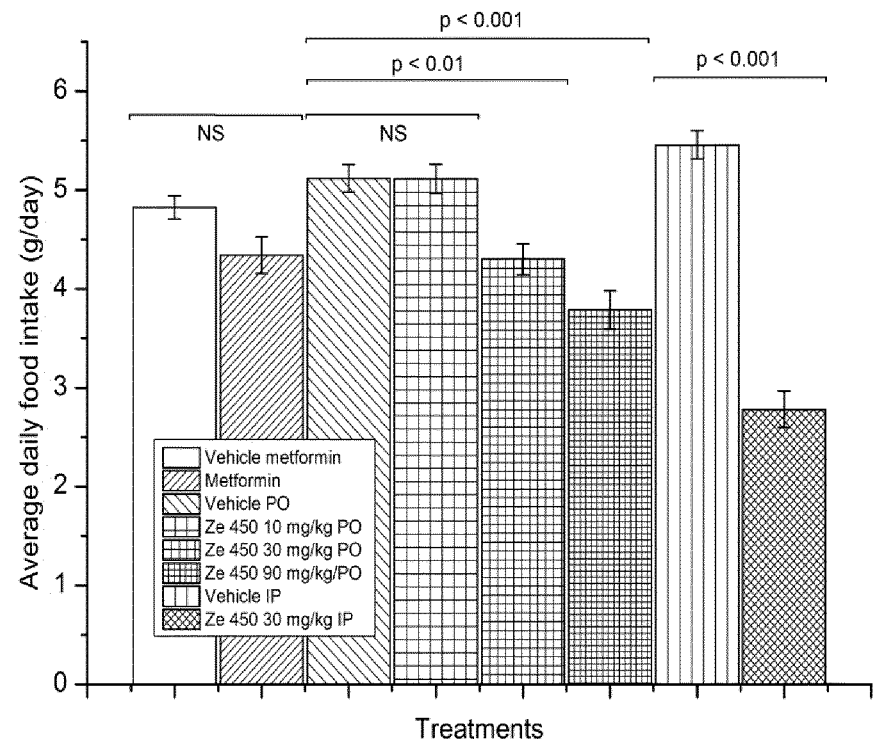
FIG. 3 is a column graph illustrating the average daily food intake (g/day) (significant differences vs. respective vehicles: $*p<0.05$, $p<0.01$, $*p<0.001$).
Figure 4:
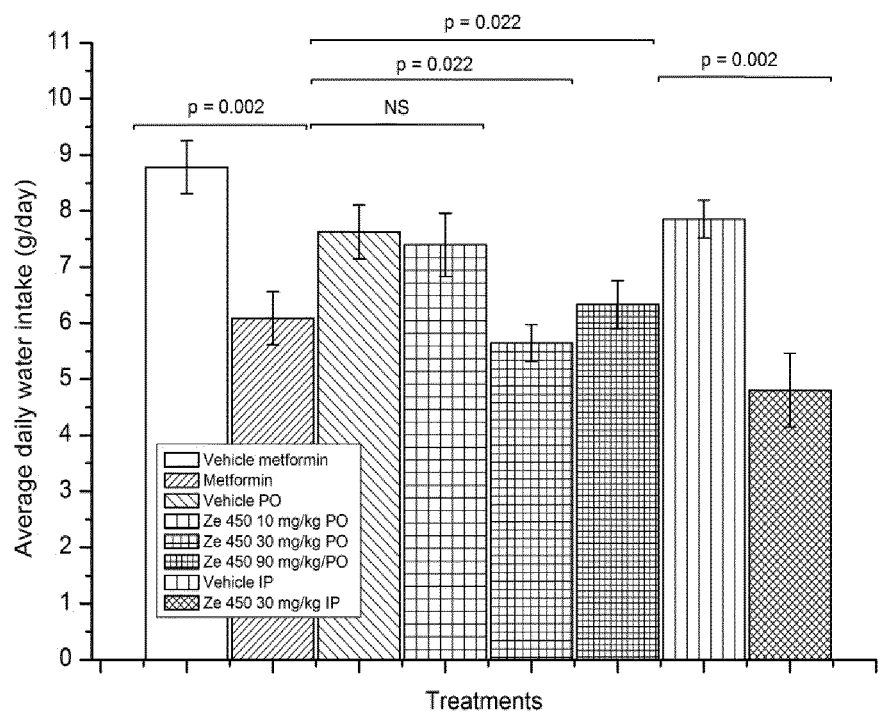
FIG. 4 is a column graph illustrating the average daily water intake (g/day).

The reduction in body weight coincides with by a significant reduction in food intake (see FIG. 3).

The largest reduction in food intake was observed in the group, which received IP injection of 30 mg/kg/day Ze 450. This indicates that the reduction in food intake observed in the PO groups was not due to local irritation of the upper GI tract of the animals and adversely avoidance of food.

A very sensitive marker effect for an anti-diabetic action is the reduction in water intake. Metformin showed a significant (p=0.002) reduction in the average weekly water intake. In the two highest doses of Ze 450 for PO administration (30 mg/kg and 90 mg/kg daily) a comparable reduction in water intake was observed (P=0.022). The largest reduction was observed after IP administration of 30 mg/kg/day Ze 450.

Figure 5A:
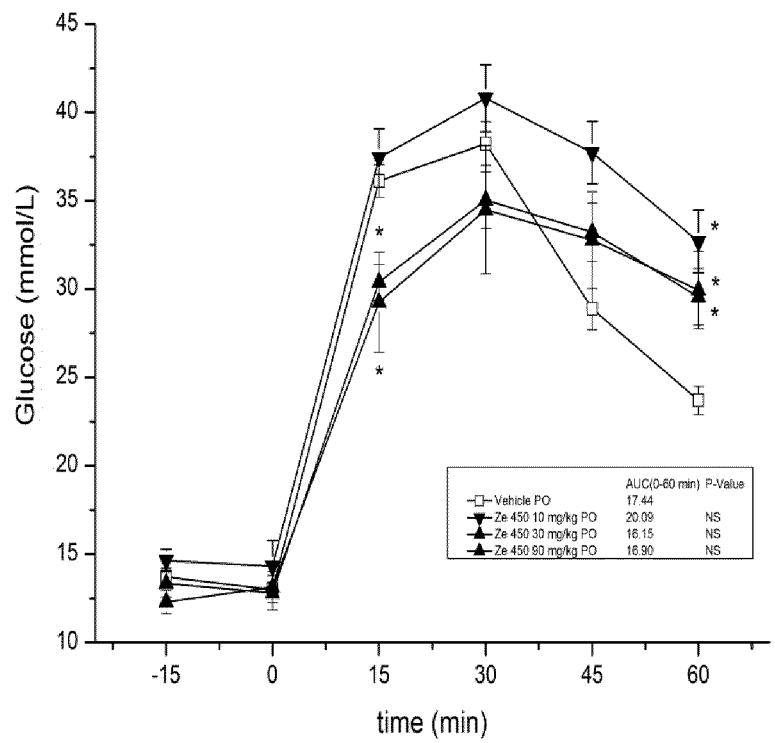
FIGS. 5a and b are graphs showing the glucose concentration (mmol/L) during the oral glucose tolerance test (OGTT).
Figure 5B:
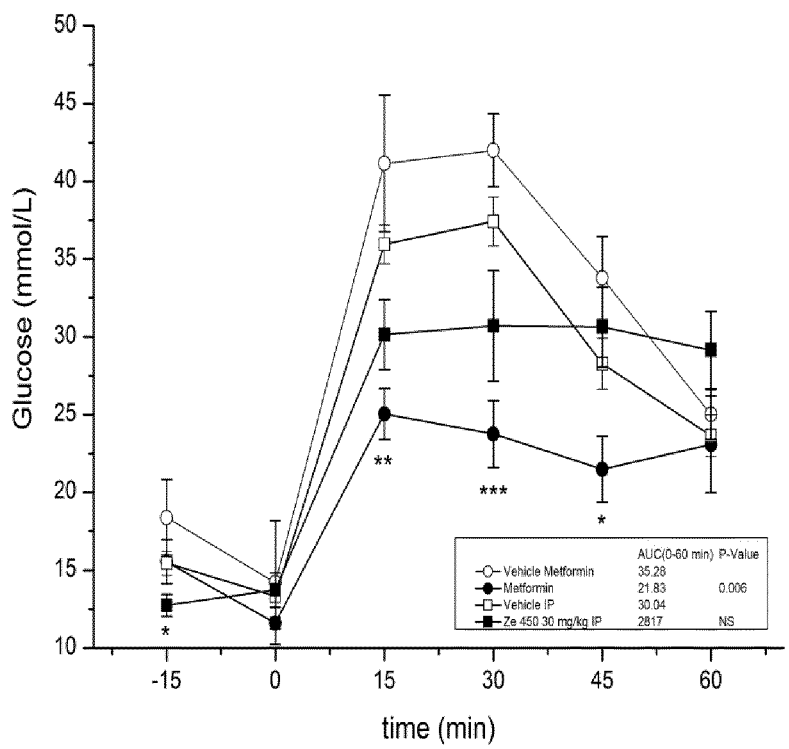
FIG. 5b shows the effects of metformin and IP Ze 450 administration (significant differences vs. respective vehicles: $*p<0.05$, $p<0.01$, $*p<0.001$).

The effects on glucose and insulin response to an oral bolus of glucose during an OGTT are shown in FIGS. 5 and 6. Ze 450 PO treatment significantly reduced the increase in glucose concentration during the first 30 min of the OGTT in the middle (10 mg/kg) and high (30 mg/kg) dose groups. Compared to the control (vehicle) the profile of the glucose concentration/time curve was prolonged, which was statistically significant (p<0.05) at 60 min. for all oral Ze 450 treatments (FIG. 5a). This was also clearly evident for the IP Ze 450 treatment where average glucose concentrations were virtually unchanged from 15 to 60 min. after start of the OGTT. Metformin effects on glucose were similar as the effects of the IP administration of Ze 450 (FIG. 5b).

Figure 6A:
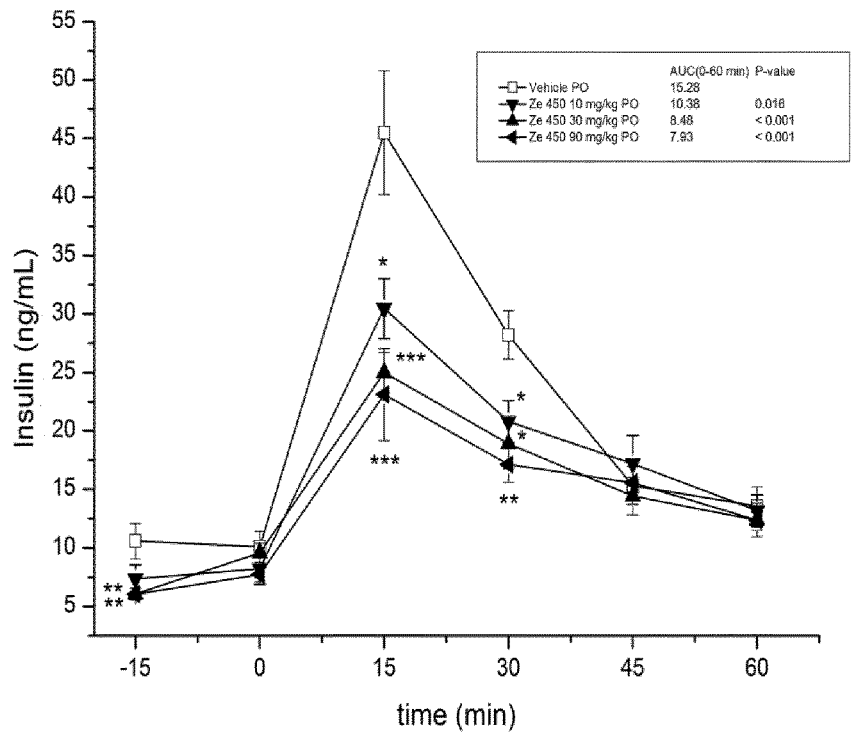
FIGS. 6a and b are graphs showing the insulin concentration (ng/ml) during the oral glucose tolerance test (OGTT).
Figure 6B:
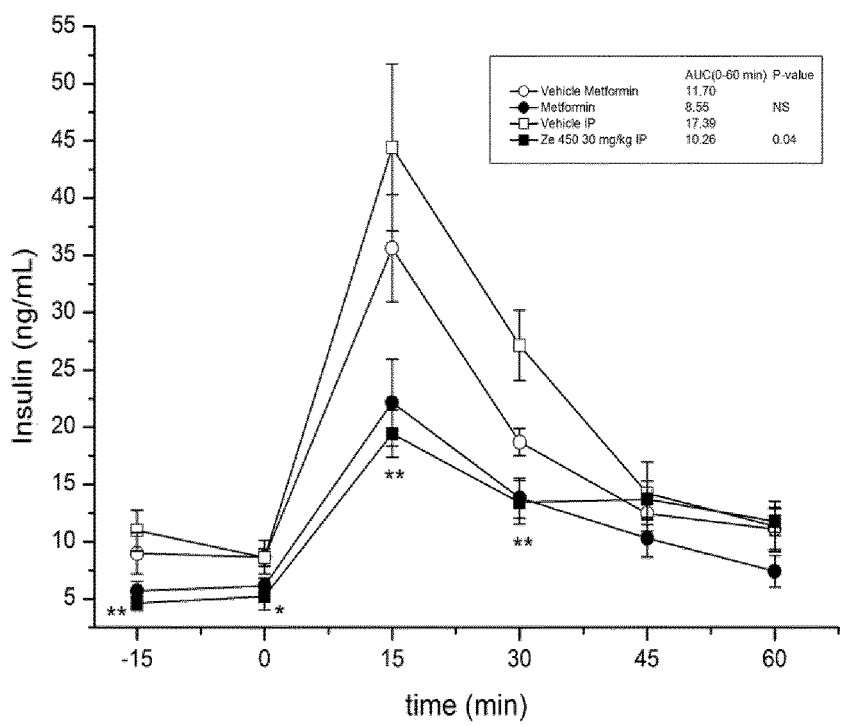
FIG. 6b shows the effect of metformin and IP administration of Ze 450 (significant differences vs. respective vehicles: $*p<0.05$, $p<0.01$, $*p<0.001$).

The effects of the treatments on insulin concentrations are shown in FIGS. 6a and 6b.

Each of the oral administrations of Ze 450 significantly decreased glucose concentrations compared to vehicle control. The decrease was dose-dependent, however not dose-proportional. The dose of 30 mg/kg Ze 450 showed almost a maximum effect which was not significantly further increased by increasing the dose to 90 mg/kg. Similar effects were seen with metformin and Ze 450 IP administration.

The effects of the above-described experiments in ob/ob mice are summarized as follows. Ze 450 has qualitatively anti-diabetic effects similar to metformin:

Orally administered Ze 450 results in a significant and dose-dependent decrease in body-weight.

Said decrease coincides with a significant and dose-dependent decrease in food-intake. Both effects (reduction in weight gain and decrease in food intake) are further enhanced by IP administration of Ze 450, which indicates a) that the active principle has a reduced oral bioavailability and b) that the decrease in food intake is the results of endocrine or central effects rather than local irritation in the upper gastrointestinal tract and subsequent food avoidance.

Ze 450 significantly decreased water intake in a dose-dependent manner which is consistent with the typical effects of oral anti-diabetic drugs.

Ze 450 exhibits glucose-normalizing effects after an oral bolus of glucose in the OGTT: peak concentrations are significantly diminished and the glucose concentration/time profile is prolonged.

Ze 450 significantly decreases the insulin response to a glucose bolus during the OGTT.

Ze 450 induces modulation of glucose and insulin response during the OGTT, which represents a significant improvement of glucose metabolism, homeostasis and an improved sensitivity to insulin.

Therefore, it has been proven in an established and representative animal model for diabetes in vivo that an extract from *Cimicifuga* sp. as represented by extract Ze 450 has significant anti-diabetic effects in mammals.

The invention claimed is:

1. A method of treatment of diabetes mellitus type 2, the method comprising orally administering to a mammal with diabetes mellitus type 2 an effective amount of an extract from *Cimicifuga racemosa*, wherein the extract is effective for the treatment of diabetes mellitus type 2.

2. The method of claim 1, wherein the extract is prepared by a method comprising the steps:
   (i) providing plant material from *Cimicifuga racemosa*,
   (ii) treating the plant material with an extraction agent, and
   (iii) concentrating the extract.

3. The method of claim 2, wherein the extract resulting from (ii) is concentrated in the presence of a solution mediator.

4. The method of claim 1, wherein the extract of *Cimicifuga racemosa* is formulated for oral administration.

5. The method of claim 3, wherein the solution mediator is an organic polymer capable of being colloidally dispersible or soluble in the extraction agent.

6. The method of claim 5, wherein the solution mediator is an organic polymer having an average molecular mass of at least about 1000 Dalton units.

7. The method of claim 6, wherein the solution mediator is polyvinylpyrrolidone (PVP).

* * * * *